(12) United States Patent
Syed (10) Patent No.: US 11,672,681 B2
(45) Date of Patent: Jun. 13, 2023

(54) VARIABLE FLOW STENT

(71) Applicant: Mubin I. Syed, Springfield, OH (US)

(72) Inventor: Mubin I. Syed, Springfield, OH (US)

( * ) Notice: Subject to any disclaimer, the term of this patent is extended or adjusted under 35 U.S.C. 154(b) by 711 days.

(21) Appl. No.: 16/726,775

(22) Filed: Dec. 24, 2019

(65) Prior Publication Data

US 2020/0237538 A1 Jul. 30, 2020

Related U.S. Application Data

(60) Provisional application No. 62/797,493, filed on Jan. 28, 2019.

(51) Int. Cl.
| | | |
|---|---|---|
| *A61F 2/90* | (2013.01) | |
| *A61F 2/07* | (2013.01) | |
| *A61B 17/12* | (2006.01) | |
| *A61F 2/915* | (2013.01) | |
| *A61B 17/34* | (2006.01) | |
| *A61B 17/11* | (2006.01) | |
| *A61B 90/00* | (2016.01) | |

(52) U.S. Cl.
CPC .......... *A61F 2/90* (2013.01); *A61B 17/12136* (2013.01); *A61B 17/12168* (2013.01); *A61F 2/07* (2013.01); *A61B 17/3498* (2013.01); *A61B 2017/1139* (2013.01); *A61B 2017/3464* (2013.01); *A61B 2017/3486* (2013.01); *A61B 2090/3966* (2016.02); *A61F 2/915* (2013.01); *A61F 2002/91533* (2013.01); *A61F 2002/91558* (2013.01); *A61F 2230/0054* (2013.01)

(58) Field of Classification Search
CPC ........ A61F 2/07; A61F 2/90; A61B 17/12168; A61B 17/3498; A61B 17/12136; A61B 2017/1139; A61B 2017/3486
See application file for complete search history.

(56) References Cited

U.S. PATENT DOCUMENTS

| | | | | |
|---|---|---|---|---|
| 5,693,088 | A | * | 12/1997 | Lazarus .................. A61F 2/844 623/1.35 |
| 5,766,192 | A | | 6/1998 | Zacca |
| 5,997,563 | A | | 12/1999 | Kretzers |
| 6,277,136 | B1 | * | 8/2001 | Bonutti .............. A61B 17/0218 606/190 |
| 6,764,505 | B1 | | 7/2004 | Hossainy et al. |
| 6,932,829 | B2 | | 8/2005 | Majercak |
| 7,651,520 | B2 | | 1/2010 | Fischell et al. |

(Continued)

*Primary Examiner* — Katherine H Schwiker
(74) *Attorney, Agent, or Firm* — Jennifer Hayes; Nixon Peabody LLP (57) ABSTRACT

A variable flow stent is described for use with AV fistulas, TIPS procedures or dialysis grafts. The flow may be varied by adjusting the diameter of the stent. Embodiments include: a covered stent having a secondary chamber that functions as an air or fluid bladder; an expandable chamber within an interior stent covering; a retractable jack device with hooks that engage (snag) opposing walls of the stent; and, a stent with a hollow chamber or pocket in the interior stent covering into which an expandable balloon can be inserted. A self-healing valve is described for inflating or deflating expandable elements within the stent and may be implemented using a self-healing membrane. A radiopaque collar may be used to provide a marker surrounding the self-healing valve. If under-shunting or over-shunting occurs over time, the variable diameter stent may be adjusted using a second procedure.

16 Claims, 10 Drawing Sheets

(56) References Cited

U.S. PATENT DOCUMENTS

| | | |
|---|---|---|
| 7,674,493 B2 | 3/2010 | Hossainy et al. |
| 7,740,791 B2 | 6/2010 | Kleine et al. |
| 7,828,832 B2 | 11/2010 | Belluche et al. |
| 8,119,184 B2 | 2/2012 | Hossainy et al. |
| 8,728,144 B2 | 5/2014 | Fearnot |
| 9,060,890 B2 | 6/2015 | Bingener-Casey et al. |
| 9,855,705 B2 | 1/2018 | Wang et al. |
| 2001/0023369 A1* | 9/2001 | Chobotov ............... A61F 2/06 623/1.11 |
| 2001/0053882 A1 | 12/2001 | Haddock et al. |
| 2002/0049402 A1 | 4/2002 | Peacock et al. |
| 2002/0165598 A1* | 11/2002 | Wahr ............... A61B 17/12136 623/1.11 |
| 2004/0111143 A1 | 6/2004 | Fischell et al. |
| 2012/0239137 A1 | 9/2012 | Heuser et al. |
| 2014/0249565 A1 | 9/2014 | Laine et al. |
| 2015/0297818 A1 | 10/2015 | Matsubara et al. |
| 2016/0175087 A1 | 6/2016 | Heuser et al. |
| 2018/0207408 A1 | 7/2018 | Neal |

\* cited by examiner

101
inserting a variable covered stent comprising a cylindrical wire mesh and an interior stent cover, the interior stent cover comprising an inflatable secondary chamber and a self-healing valve coupled to the secondary chamber, wherein a radiopaque collar is concentrically disposed around the one-way valve;

102
inserting a catheter percutaneously into the blood vessel;

103
delivering an inflation device through the catheter;

104
locating the one-way valve using the radiopaque collar;

105
penetrating the one-way valve with the inflation device;

106
inflating the secondary chamber using the inflation device to narrow the interior stent cover; and, 107
withdrawing the catheter and inflation device from the blood vessel.

FIG. 10

VARIABLE FLOW STENT

CROSS-REFERENCE TO RELATED APPLICATIONS

The present patent application claims priority to provisional application No. 62/797,493, entitled "Variable Flow Stent", filed Jan. 28, 2019, the entirety of which is herein incorporated by reference.

TECHNICAL FIELD

This invention relates to variable flow stents, and in particular to variable flow stents that may be adjusted using a second procedure or adjusted directly using a needle through the skin.

BACKGROUND

A transjugular intrahepatic portosystemic shunt (TIPS) procedure may be used to alleviate hypertension in the portal vein. This hypertension is usually caused by liver cirrhosis due to alcohol, nonalcoholic steatohepatitis (NASH), or infectious hepatitis amongst other problems. The shunt may be used to reduce internal bleeding in the stomach and esophagus in patients with cirrhosis. The portal hypertension is relieved by diverting blood in the portal vein into general circulation.

Although diverting portal venous blood into general circulation may be beneficial for reducing internal bleeding it is toxic to the patient, to a variable degree depending on the diameter of the stent. A balance is required between internal bleeding and toxic effects.

Use of variable flow stents may be also be advantageous for treatment of arterio venous (AV) fistulas or for dialysis treatments.

Accordingly, there is a need in the art for variable flow stents, and for a reliable method for adjusting the diameter of a variable flow stent. The adjustment may be required during the initial intervention or a following intervention.

SUMMARY

In accordance with a first aspect of the invention, a variable flow stent for insertion in a blood vessel is disclosed that includes a cylindrical wire mesh; a cylindrical cover disposed inside the cylindrical wire mesh; a secondary chamber inside the cylindrical cover configurable as an air bladder, expandable when inflated; a self-healing valve disposed in an interior wall of the secondary chamber; a radiopaque collar concentrically disposed around the self-healing valve for assistance in locating the self-healing valve; wherein a catheter may be percutaneously inserted into the blood vessel and the secondary chamber inflated through the self-healing valve to narrow the main lumen of the variable diameter stent.

The catheter may be configurable to insert and operate a side firing curved needle.

The self-healing valve may include a self-healing membrane.

The variable flow stent may be configured to controllably limit blood flow in a transjugular intrahepatic portosystemic shunt (TIPS).

The variable flow stent may be configured to controllably limit blood flow in a dialysis graft or a fistula.

In accordance with a second aspect of the invention, a variable flow stent for insertion in a blood vessel is disclosed that includes a cylindrical wire mesh having an interior stent cover; an expandable chamber in the interior stent cover; a self-healing valve disposed in an interior wall of the expandable chamber; a radiopaque collar concentrically disposed around the self-healing valve for assistance in locating the self-healing valve; a balloon insertable into the expandable chamber using a catheter equipped with a pre-curved NITINOL needle or using an OUTBACK type reentry device; wherein the balloon is inflatable through the self-healing valve to expand the expandable chamber and narrow the main lumen of the variable diameter stent.

The self-healing valve may include a self-healing membrane.

The inflated balloon may be long and narrow, at least 3 mm in length.

In accordance with a third aspect of the invention, a method for deploying a variable flow stent in a blood vessel is disclosed that includes providing a cylindrical wire mesh; providing a secondary chamber within the cylindrical wire mesh configurable as an air bladder or balloon, expandable when inflated; providing a self-healing valve disposed in an interior wall of the secondary chamber; providing a radiopaque collar concentrically disposed around the self-healing valve; providing a catheter; inserting the catheter percutaneously into the blood vessel; delivering through the catheter an inflation device; locating the self-healing valve using the radiopaque collar; penetrating the self-healing valve with a curved needle portion of the inflation device; inflating the secondary chamber using the inflation device, thereby narrowing the main lumen of the variable flow stent: and, withdrawing the catheter and all procedural devices from the blood vessel.

The curved needle may be NITINOL.

The catheter may be configurable to insert and operate a side firing curved needle.

In accordance with a fourth aspect of the invention, a further method for deploying a variable flow stent in a blood vessel is disclosed that includes providing a covered stent having an exterior cover over a cylindrical wire mesh; inserting a catheter percutaneously into the blood vessel, delivering an expandable jack device through the catheter; expanding the expandable jack device to snag opposing mesh walls of the cylindrical wire mesh; retracting the expandable jack device to narrow the lumen of the stent portion of the covered stent; disengaging the expandable jack device from the opposing mesh walls; and, withdrawing the catheter and the expandable jack device from the blood vessel. In a subsequent procedure a catheter may be reinserted percutaneously into the blood vessel for inserting a balloon, and the balloon may be inflated to re-narrow or widen the lumen of the variable flow stent. Alternatively, loops extending into the interior of the wire mesh cylinder may be provided. The loops may be used to engage both the wire mesh cylinder and the outer stent cover. The microhooks may be configured to engage with the loops using a counterclockwise twist of the expandable jack device and disengage with a clockwise twist for example.

In accordance with a fifth aspect of the invention, a further method for deploying a variable flow stent in a blood vessel is disclosed that includes advancing a variable covered stent into a blood vessel that may be located superficially within a patient's body, surgically implanting a port at a location reachable by a needle, and coupling the variable covered stent to the surgically implanted port by connecting a catheter between them. A secondary chamber in the variable covered stent may be controllably inflated or deflated using a needle injected into the surgically implanted port to respectively narrow or widen the lumen of the variable covered stent.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

DETAILED DESCRIPTION

A variable flow stent is described for use with AV fistulas, TIPS procedures or dialysis grafts. It may be used for other vascular interventions. The flow may be varied by adjusting the diameter of the stent. Embodiments include: a covered stent having a secondary chamber that functions as an air or fluid bladder; an expandable chamber within an interior stent covering; a retractable jack device with hooks that engage (snag) opposing walls of the stent; and, a stent with a hollow chamber or pocket in the interior stent covering into which an expandable balloon can be inserted. A self-healing valve is described for inflating or deflating expandable elements within the stent and may be implemented using a self-healing membrane. A radiopaque collar may be used to provide a marker surrounding the self-healing valve. If under-shunting or over-shunting occurs over time, the variable diameter stent may be adjusted using a second procedure.

Figure 1A:
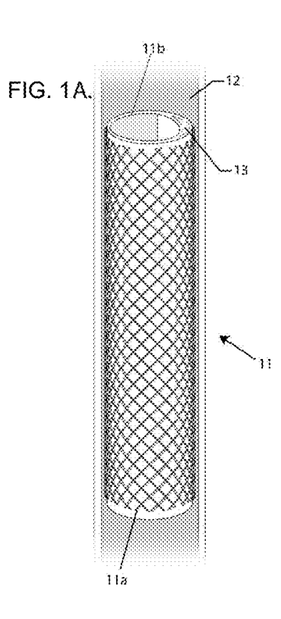
FIGS. 1A-1C are three-dimensional cut away views illustrating a TIPS procedure using a long chamber option, wherein a secondary chamber is expanded when inflated, in accordance with embodiments of the invention.
Figure 1B:
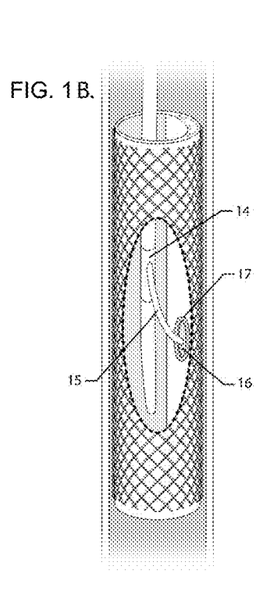
Figure 1C:
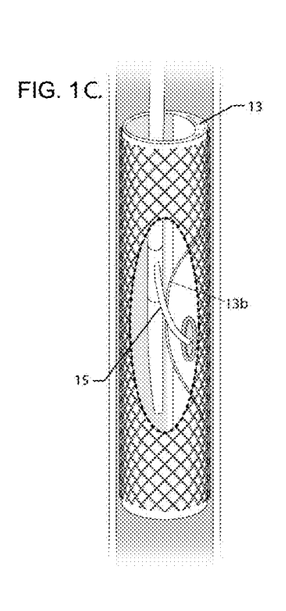

FIGS. 1A-C depict a three-part process for inserting a transjugular intrahepatic portosystemic shunt (TIPS) in a long chamber embodiment. In FIG. 1A, a covered stent 11 is shown inside a blood vessel 12. Covered stent 11 includes an outer wire mesh 11a and a cover 11b. As shown in FIGS. 1A-1C, the cover 11b is disposed on an interior of the cylindrical, outer wire mesh 11a.

The wire mesh 11a of the stent in this and other embodiments may comprise NITINOL or other shape memory material if the stent is self-expanding, taking advantage of the spring-like characteristic of a shape memory material. The wire mesh may also comprise wires of stainless steel or other metal alloy; in this case the stent may be balloon adjustable wherein the wire mesh will conform to the shape of the balloon as it inflates.

The cover 11b may comprise polytetrafluoroethylene (PTFE) or another synthetic fluoropolymer. Synthetic polymers may be effective in limiting neointimal hyperplasia, which can result in vascular wall thickening following an intervention. The cover 11b may also comprise an elastic fabric such as DACRON.

The wire mesh 11a may be attached or bonded to the cover using 11b many different methods, as known in the art, including, for example, electrospinning, layer-by-layer assembly, casting, polymer sleeve braiding, riveting and suturing.

An expandable secondary chamber 13 is provided in the cover 11b. In one embodiment, secondary chamber 13 is provided by adding a wall or additional piece of material to the interior cover 31b. The wall or additional piece of material may be made of the same material or a different material than the interior cover 11b. For example, the wall that forms the secondary chamber 13 may comprise an elastic material such as a medical grade rubber as used in a standard Fogarty balloons.

Secondary chamber 13 functions as an air bladder or balloon and is shown in its deflated form in FIGS. 1A and 1B and is shown in its inflated form 13b in FIG. 1C. A radio-opaque collar 17 may be used to help guide the placement of side-firing curved needle 15 to the entry region 16. Radio-opaque collars may comprise materials such as barium or iodineare, which have the property that they absorb X-rays. The entry region 16, inside of radiopaque collar 17, may comprise a self-healing elastic membrane that will close after penetration by a needle such as side firing curved needle 15.

Side-firing curved needle 15 may be introduced via catheter 14 and be positioned adjacent entry region 16, then penetrate the entry region to fill the secondary chamber. It will be appreciated that the self-healing elastic membrane 16 may be punctured externally or endovascularly by the needle 15.

The self-healing elastic membrane 16 may comprise butyl rubber or may also comprise microcapsules filled with an adhesive, wherein if the microcapsules are penetrated or broken the adhesive flows to repair the associated damage. The butyl rubber may be biocompatible. Valves with such self-healing characteristics are commonly found in introducer sheaths.

In FIG. 1C, secondary chamber 13 is shown inflated 13b using the side-firing curved needle 15, narrowing the main lumen of the covered stent. In a subsequent procedure, the depicted narrowing of the main lumen may be increased or decreased by inflation or deflation respectively, as may be required for a desired balance between internal bleeding and blood toxicity. The required balance may vary over time, making such adjustments necessary in some cases.

Figure 2A:
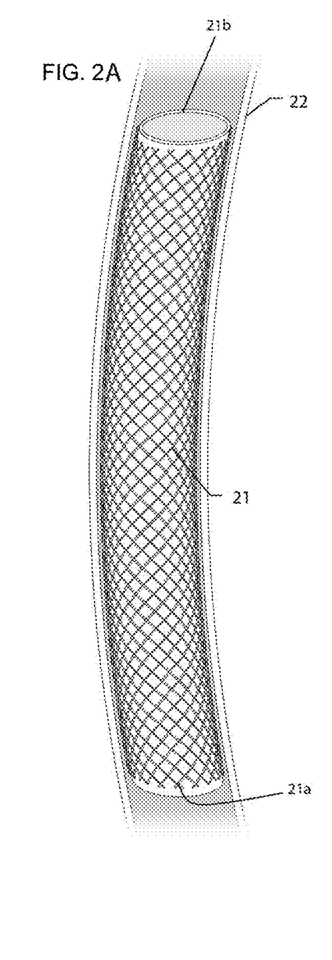
FIGS. 2A-2C are three-dimensional cut away views illustrating a TIPS procedure using a pocket chamber option, wherein a balloon is deployed into an expandable chamber in an interior stent covering, in accordance with embodiments of the invention.
Figure 2B:
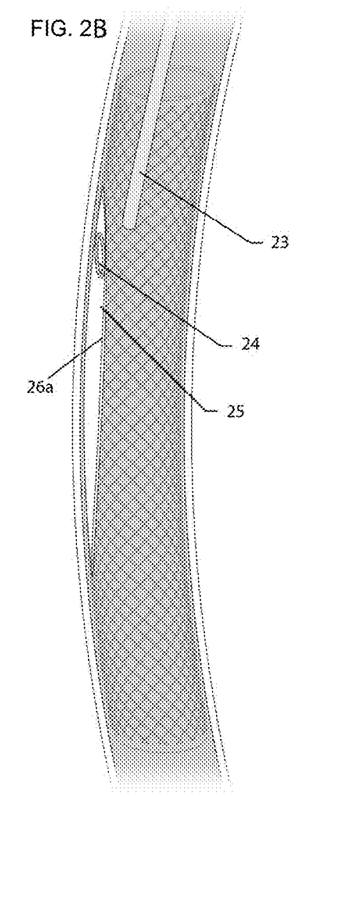
Figure 2C:
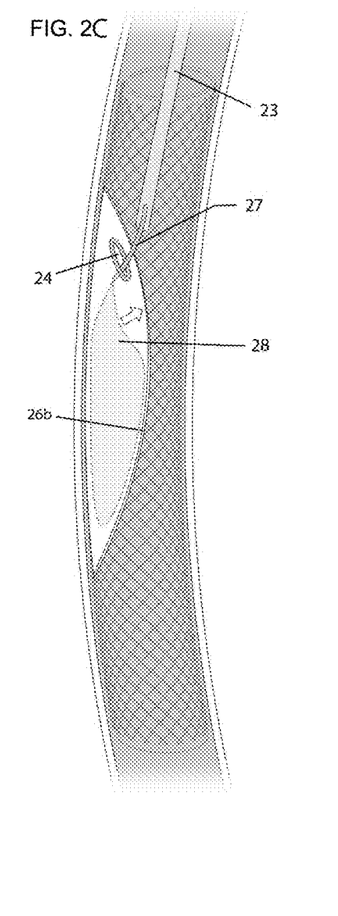

FIGS. 2A-C depict a three-part process for inserting a transjugular intrahepatic portosystemic shunt (TIPS) in a pocket chamber embodiment, wherein the pocket chamber is another form of secondary chamber. In FIG. 2A, a covered stent 21 is shown inside a blood vessel 22. Covered stent 21 includes a cylindrical wire mesh 21a and an internal cover 21b. The cover 21b is disposed on an interior of the cylindrical wire mesh 21a, as described above.

In FIG. 2B, a sheath 23 is positioned in the blood vessel to target a self-healing valve 24 disposed in a secondary chamber 25 having an internal wall 26a. Sheath 23 may be a metal sheath for containing the pre-curved needle 27 and may be relatively straight in this region of blood vessel 22. Sheath 23 may also comprise a thermoplastic elastomer such as PEBAX. As with the previous embodiment, the self-healing valve 24 may include a self-healing membrane and may be provided with a radio opaque collar for assistance in guiding sheath 23 to the valve 24. The wall 26a may be made from the same material or a different material than the cover 21b. In some embodiments, the wall 26a is made of an expandable material. For example, the wall may be made of butyl rubber. The secondary chamber 25 is accessible via self-healing valve 24.

In FIG. 2C, a pre-curved needle 27 advances through sheath 23, reverts to its curved shape, and penetrates self-healing valve 24. In some embodiments, the pre-curved needle 27 may be made from NITINOL. NITINOL is a shape memory alloy. It will be appreciated that other shape memory materials may be used for the pre-curved needle 27.

A balloon 28 may be provided in the secondary chamber 25. The balloon 28 may be delivered by the pre-curved needle or may be part of the covered stent 21 that is delivered to the blood vessel (i.e., the balloon may be permanently provided in the secondary chamber 25). The balloon 28 is accessed through curved needle 27 deployed via sheath 23 and inflated to narrow the main lumen of the covered stent 21 as shown in FIG. 2C. The internal wall 26b of the secondary chamber has expanded as shown. Balloon 28 may comprise KEVLAR or polyethylene terephthalate (PET) or nylon as examples. Sheath 23 is removed after the balloon has been inflated.

In a subsequent procedure, the depicted narrowing of the main lumen may be increased or decreased by inflation or deflation respectively of balloon 28, accessed through the pre-curved needle 27, as may be required for a desired balance between internal bleeding and blood toxicity. The balance may vary over time, making such adjustments necessary.

Figure 3A:
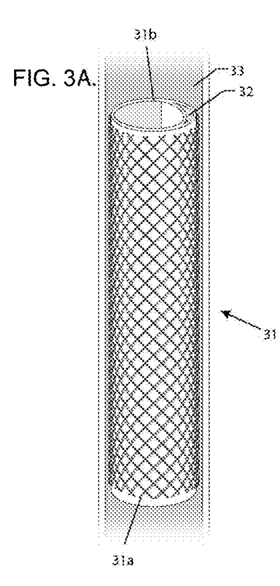
FIGS. 3A-3C are three-dimensional cut away views illustrating a TIPS procedure using a long balloon option, wherein a long narrow balloon is deployed into an expandable chamber in an interior stent covering, in accordance with embodiments of the invention.
Figure 3B:
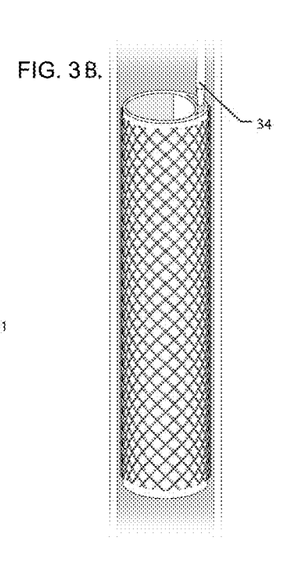
Figure 3C:
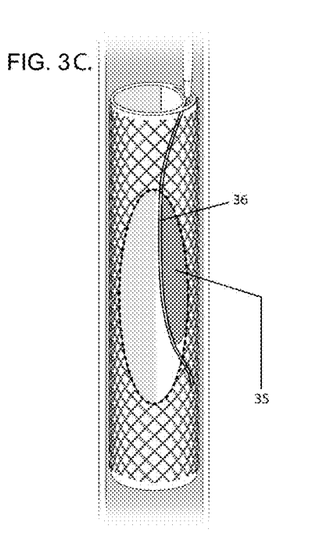

FIGS. 3A-C depict a three-part process for inserting a transjugular intrahepatic portosystemic shunt (TIPS) in a long balloon embodiment. In FIG. 3A, a covered stent 31 having a secondary chamber is inserted into a blood vessel 33. Covered stent 31 includes a wire mesh 31a and an interior cover 31b. In FIG. 3B, a sheath 34 containing an expandable balloon is shown entering an entry region 32 of the interior cover 31b to access the secondary chamber. In FIG. 3B, the entry region 32 is shown as being crescent-shaped. The entry region 32 may comprise a self-healing valve as described in reference to FIGS. 1 and 2, and sheath 34 may include a sharp point for penetrating the entry region 32. In FIG. 3C, a long narrow balloon 35 is expanded into the secondary chamber, narrowing the primary chamber of the stent 31. In FIG. 3C, the secondary chamber is the interior cover 31b by providing an elastic wall 36 that is coupled to the interior cover 31b. The elastic wall 36 of the secondary chamber deflects, as shown in FIG. 3C, as the balloon is inflated. To achieve the desired elasticity, the wall 36 may comprise a different material than the interior cover 31b. If the balloon 35 comprises a non-thrombogenic (non-clot-forming) material it may remain permanently in the patient's body. Accordingly, balloon 35 may comprise an anti-coagulant coating such as HEPERAN or it may also comprise a laminate construction including an elastic layer and a thin non-thrombogenic layer.

In a subsequent procedure, the depicted narrowing of the primary chamber of stent 31 may be increased or decreased by inflating or deflating respectively the long narrow balloon 35, as may be required for a desired balance between over-shunting and under-shunting. Alternatively, a balloon catheter may be directly inserted into the space between the interior wall of the stent and the exterior wall of the stent. The balloon may be inflated deforming the interior wall of the stent into the lumen and narrowing the lumen. The balloon/catheter would then be removed, and the interior wall of the stent would stay deformed and protruding into the lumen. The desired balance between over-shunting and under-shunting may vary over time, making such adjustments necessary.

Figures 4A, 4B, 4C, 4D, 4E, 4F:
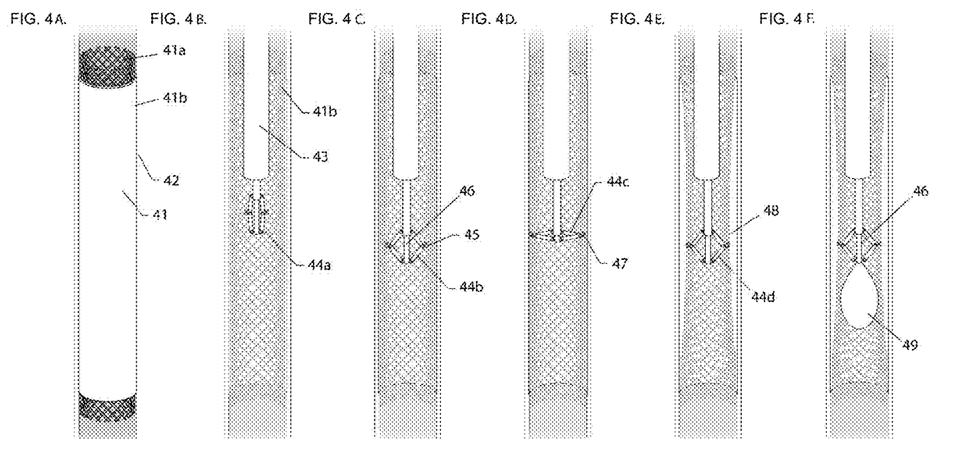
FIGS. 4A-4F are three-dimensional cut away views illustrating a TIPS procedure using an expandable jack option, wherein the jack includes microhooks for snagging the wall of the stent, in accordance with embodiments of the invention.

FIGS. 4A-F depict a six-part process for inserting a transjugular intrahepatic portosystemic shunt (TIPS) in an expandable jack embodiment. In FIG. 4A, a covered stent 41 is shown inserted into a blood vessel 42. Covered stent 41 includes a wire mesh 41a and an external cover 41b. As will be further detailed in reference to FIG. 6, the mesh wall of the stent may be affixed or bonded to the stent cover by a rivet or by welding or by other means, making the narrowed lumen reductive of blood flow.

As shown in FIG. 4A, the covered stent 41 is fully expanded. In some embodiments, the covered stent 41 is expanded by a balloon (not shown).

In FIGS. 4B-4F, the covered stent is shown cut in half in order to view the internal components, but it will be appreciated that the covered stent 41b is cylindrical as shown in FIG. 4A. As shown in FIG. 4B, a sheath 43 is deployed inside the covered stent 41. Sheath 43 includes an expandable jack device 44a, which is shown in a fully retracted form in FIG. 4B. The mechanism of the expandable jack device 44a, b, c, d may be built from parts fabricated out of stainless steel or titanium or cobalt-chrome alloy as examples. In FIG. 4C, the expandable jack device 44b is shown partially expanded. Expansion of the expandable jack device 44b may be accomplished using a threaded shaft, as might be found in a car jack. As shown in FIG. 4C, the expandable jack device 44 includes microhooks 45 that are shown distal to the shaft 46 of the expandable jack. In FIG. 4D, the expandable jack is shown in its fully expanded form 44c. Microhooks 45 may comprise stainless steel or titanium or cobalt-chrome alloy as examples. As shown in FIG. 4D, the microhooks 45 snag the mesh wall 47 of covered stent 41. In FIG. 4E, the expandable jack is partially retracted 44d to draw the snagged mesh walls inward 48, narrowing the main lumen of covered stent 41. After the lumen of covered stent 41 is narrowed as required, the expandable jack device 44 is detached from the mesh walls (to be further described) and removed.

A subsequent procedure may again snag the mesh walls and draw them further inward. During either the original procedure or a subsequent procedure shown in FIG. 4F, a balloon 49 may be deployed through the hollow shaft 46 of the jack device to widen covered stent 41 if needed. By controlling the narrowing and the widening of the covered stent 41, a desired balance may be achieved between over-shunting and under-shunting. The desired balance may vary over time, making such adjustments necessary.

Figure 5:
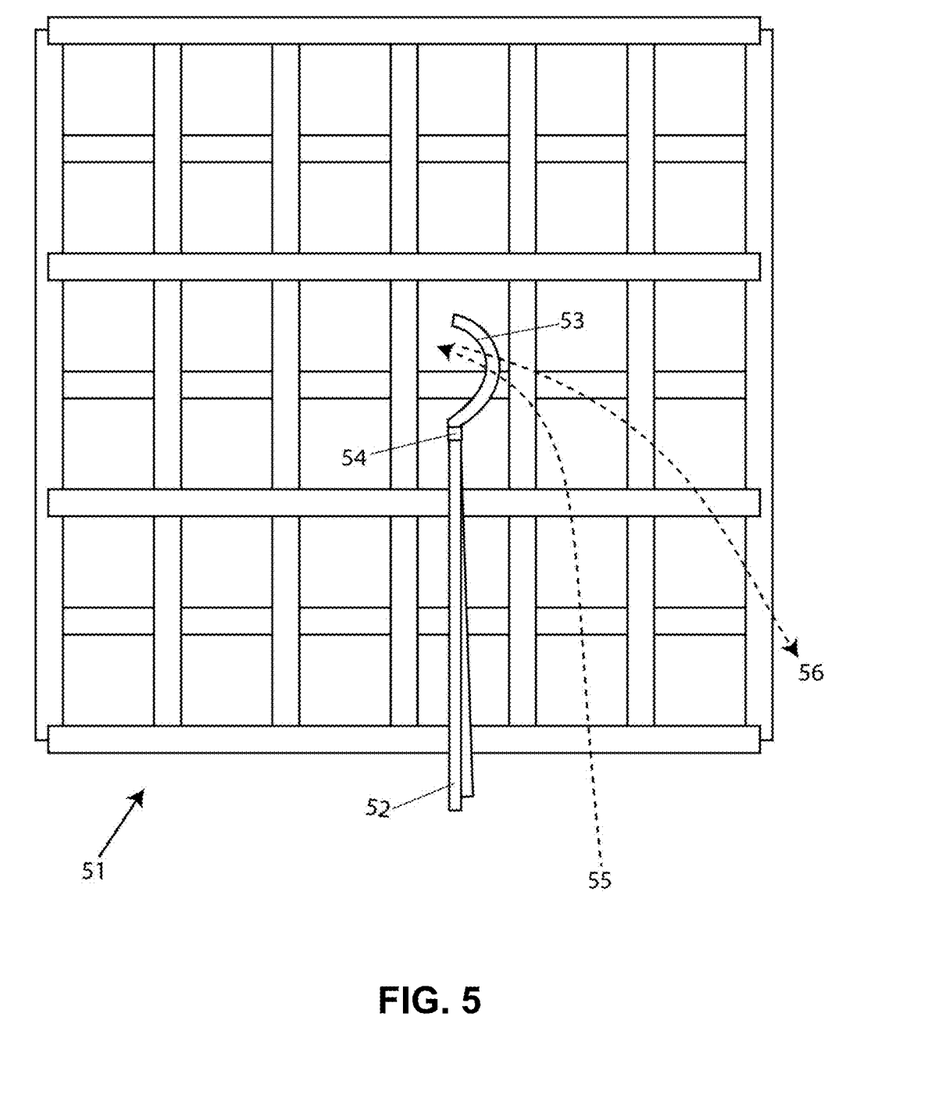
FIG. 5 illustrates a curved micro-hook together with exemplary paths for engaging in and disengaging from the wall of the stent, in accordance with embodiments of the invention.

The micro-hooks may be specially shaped to enable engagement and disengagement of the hooks with the wire mesh of the stent. FIG. 5 shows a wire mesh 51 and a pair of retractable arms 52 of the expandable jack device. The retractable arms terminate at a hinge 54 to which is attached a specially shaped micro-hook 53. Considering the curvature of micro-hook 53, engagement of the micro-hook with the wire mesh can be accomplished via micro-hook path 55. Path 55 may be accomplished via simultaneous expansion of the expandable jack device and a counterclockwise twist of the device. Disengagement of micro-hook 53 from wire mesh 51 can be accomplished via micro-hook path 56. Path 56 may be accomplished via a simultaneous contraction of the expandable jack device and a clockwise twist of the device. The interventionist may assert the clockwise or counterclockwise twisting action contemporaneously with the associated expansion or contraction of the device, as required to achieve the desired engagement or disengagement action.

Figure 6:
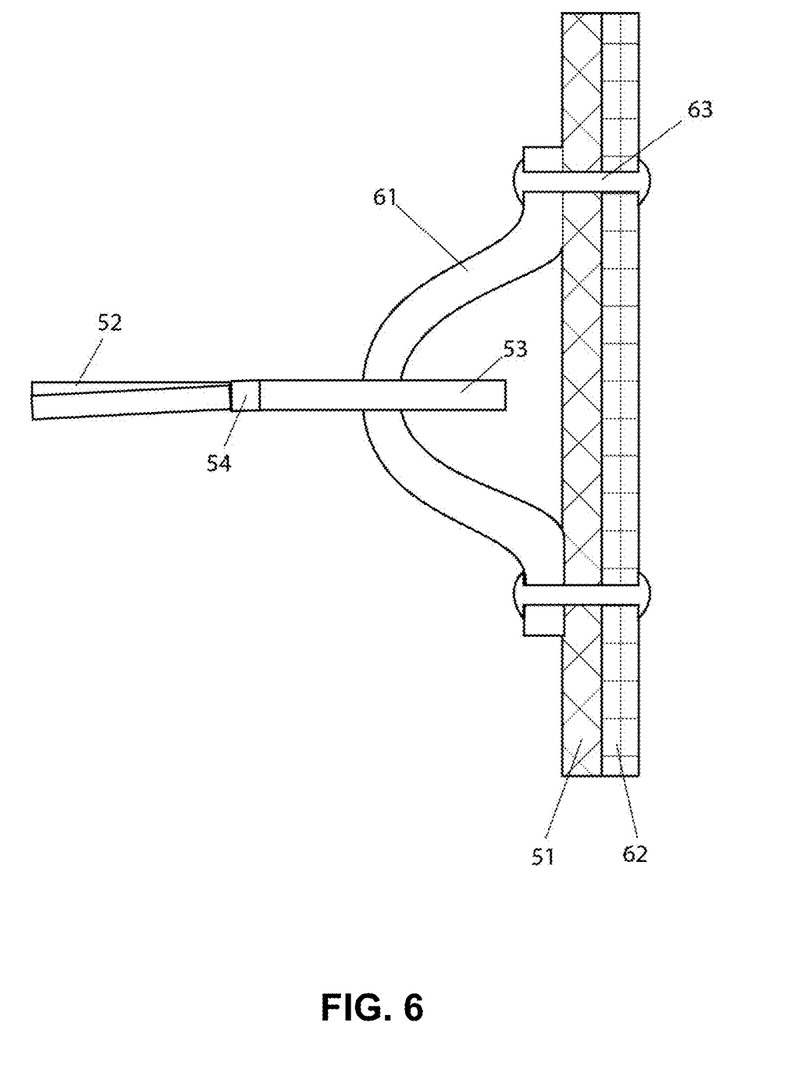
FIG. 6 illustrates engagement of a micro-hook with a loop attached to the wire mesh cylinder and to the stent cover, in accordance with embodiments of the invention.

FIG. 6 illustrates engagement of a micro-hook 53 with a loop 61 attached to the cylindrical wire mesh 51 and to the stent cover 62 using a rivet 63. Other means for connecting or bonding the three components may be used, including the use of adhesives or welding as examples. The interventionist engages micro-hook 53 with loop 61 by contemporaneously expanding the expandable jack device while applying a counterclockwise twist. The interventionist disengages micro-hook 53 from loop 61 by contemporaneously retracting the expandable jack device while applying a clockwise twist. The number of loops such as 61 provided as attachments to the cylindrical wire mesh 51 and the stent cover 62 may vary, for example, from one to eight.

Figure 7:
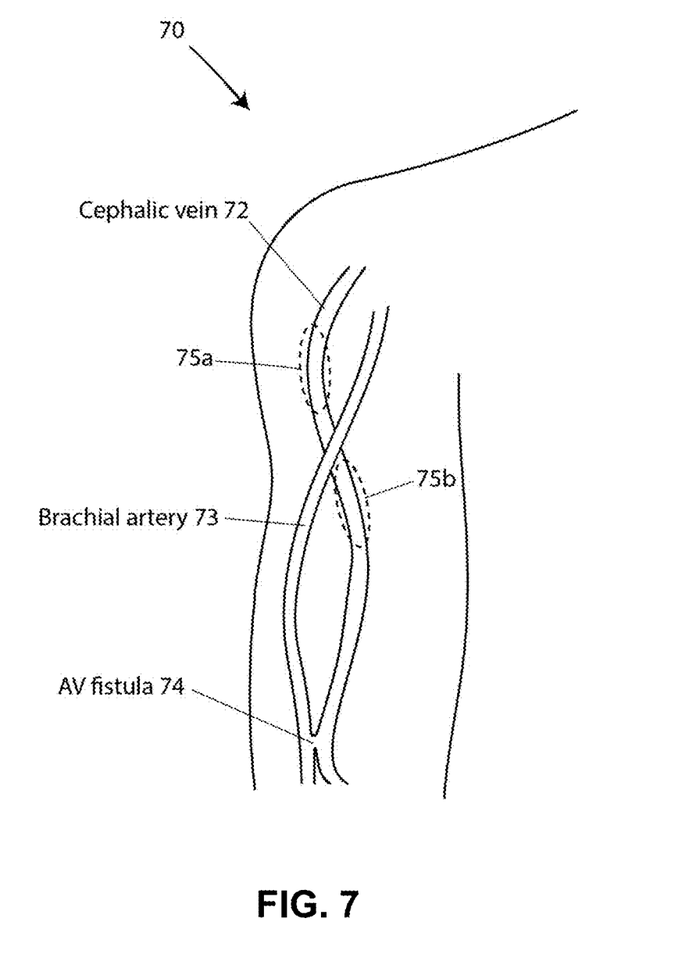
FIG. 7 depicts an AV fistula in a patient's upper arm, in accordance with embodiments of the invention.

FIG. 7 depicts blood vessels in a patient's upper arm 70. A cephalic vein 72 is shown together with a brachial artery 73, connected by an arterio venous (AV) fistula 74. The AV fistula 74 may be treated by insertion of a variable covered stent at location 75a or 75b, to be further described in reference to FIG. 8. Cephalic vein 72 and brachial artery 73 exemplify blood vessels at which an AV fistula may occur. Other combinations of veins and arteries and fistulas are covered by the present invention.

Figure 8:
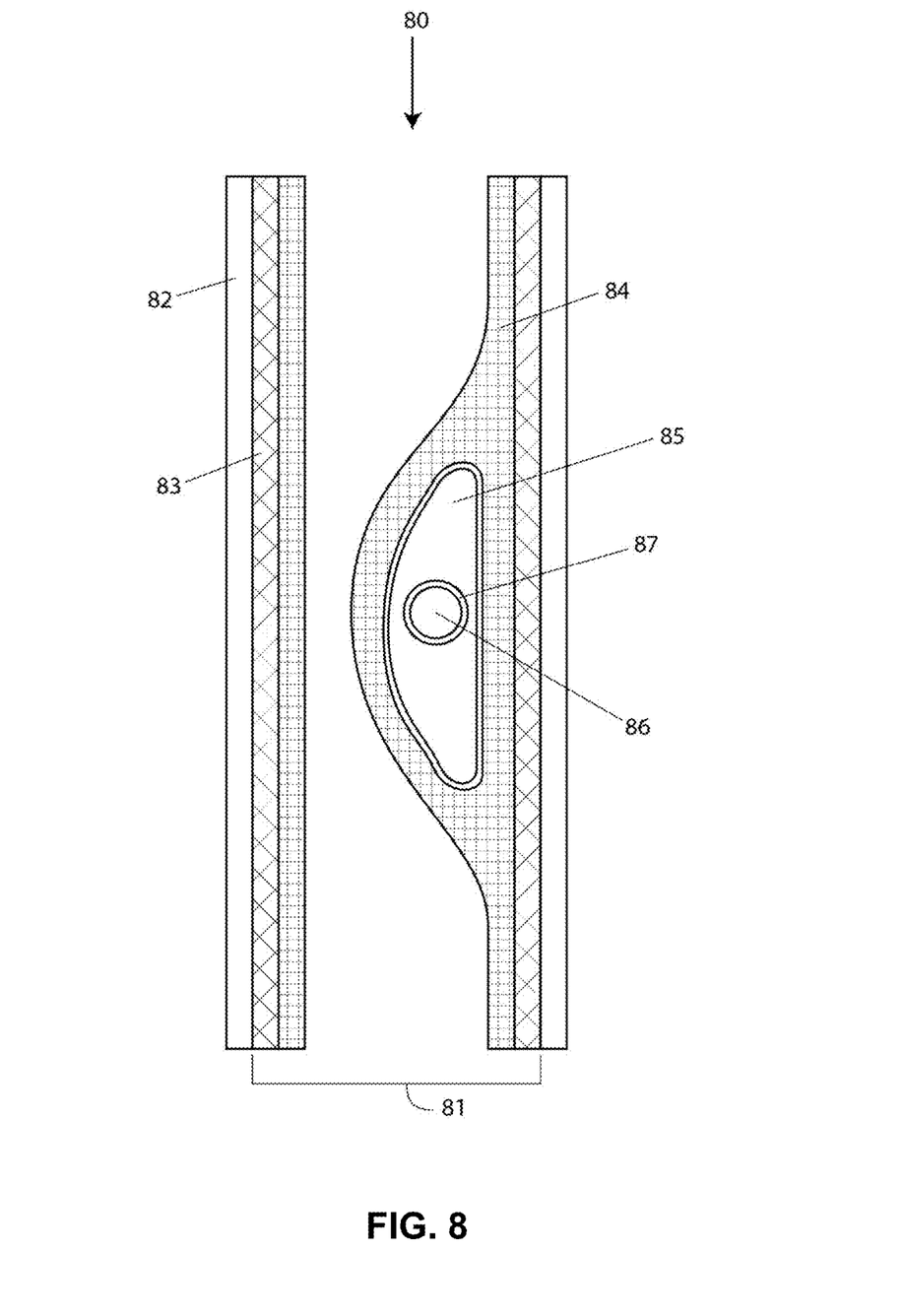
FIG. 8 illustrates an implanted variable covered stent for treatment of the AV fistula of FIG. 7, in accordance with embodiments of the invention.

FIG. 8 illustrates insertion 80 of a variable covered stent 81 in a vein 82 to treat an AV fistula, for example at location 75a, shown in FIG. 7. Covered stent 81 is positioned inside the outflow vein 82 of the fistula to be treated. Variable covered stent 81 includes a wire mesh cylinder 83 and a graft 84. Graft 84 may comprise an elastic material such as DACRON for example. Graft 84 is preconfigured with a secondary chamber 85 which is elastic and inflatable; it may comprise butyl rubber for example. Secondary chamber 85 may include a self-healing membrane valve 86, and the valve may be encircled by a radiopaque collar 87. The interventionist may locate the valve 86 using the radiopaque collar 87, and percutaneously insert a needle into the valve 86 and inflate or deflate secondary chamber 85, as required for the desired amount of venous blood flow. The interventionist may also locate the covered stent 81 and possibly the valve 86 by feel. Self-healing membrane valve 86 may be made larger in order to more easily facilitate puncture.

Figure 9:
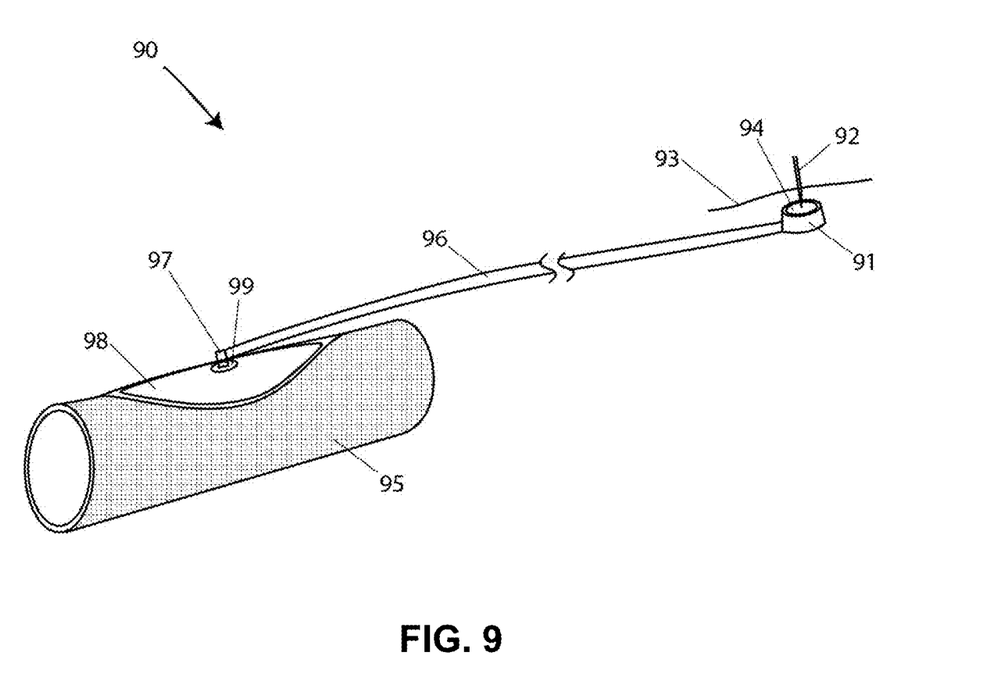
FIG. 9 illustrates a variable covered stent coupled to a surgically implanted port using a catheter to connect between them, in accordance with embodiments of the invention.

FIG. 9 illustrates the use 90 of a surgically implanted port 91, located so that a needle 92 may be percutaneously inserted through a patient's skin 93, and through a catheter entry region 94, for connecting a controllable fluid (or air) flow into a variable covered stent 95 via a catheter 96. A radiopaque collar previously described may be used to help the interventionist locate the catheter entry region 94. The catheter entry region 94 may comprise a self-healing valve. The catheter 96 provides a connection between the surgically implanted port 91 and the variable covered stent 95. A connector 97 may be used to couple the catheter 96 to a secondary chamber 98 of the variable covered stent 95. A catheter entry region 99 may be provided as shown. The secondary chamber 98 may be inflated or deflated via the needle 92, to control the lumen of the variable covered stent. Thus, an intervention may be conducted using a variable covered stent 95 positioned superficially in a patient's body while an implanted port 91 is positioned at a convenient location accessible by needle directly through the skin.

Figure 10:
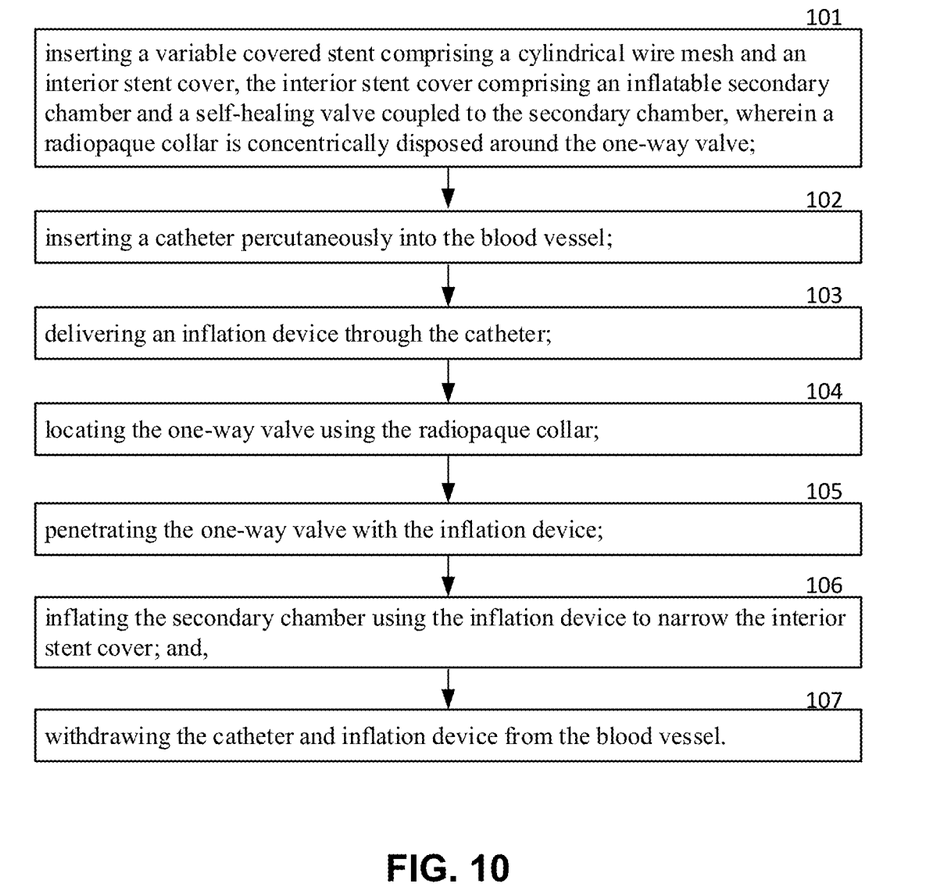
FIG. 10 is a flow chart of an exemplary process for deploying a variable diameter stent in a blood vessel in accordance with embodiments of the invention.

FIG. 10 illustrates an exemplary process that may be applied to the insertion of a transjugular intrahepatic portosystemic shunt (TIPS), or insertion of a variable covered stent adjacent an arterio venous (AV) fistula, or insertion of a variable flow stent for dialysis in accordance with embodiments of the invention. As shown in FIG. 10, the process begins by inserting a variable covered stent comprising a cylindrical wire mesh and an interior stent cover, the interior stent cover comprising an inflatable secondary chamber and a self-healing valve coupled to the secondary chamber, wherein a radiopaque collar is concentrically disposed around the self-healing valve (block 101).

The process continues by inserting a catheter percutaneously into the blood vessel (block 102). The process continues by delivering an inflation device through the catheter (block 103). The process continues by locating the self-healing valve using the radiopaque collar (block 104). The process continues by penetrating the self-healing valve with the inflation device (block 105). The process continues by inflating the secondary chamber using the inflation device to narrow the interior stent cover (block 106), and the process completes by withdrawing the catheter and the inflation device from the blood vessel (block 107).

The interventions described herein may be simplified by strategic placement of the covered stent. This may be achieved by strategic routing of the catheter into which the covered stent is inserted. If the covered stent is located at a site reachable by a percutaneously inserted needle, then for example an inflatable element can be inflated or deflated directly through the needle and through the skin. The reachable site may include an implantable port and a variable flow stent may be delivered to the implantable port. Similarly, an expandable jack device may be more easily operated via direct manipulation through a shortened percutaneous connection.

Embodiments of variable flow stents have been described for inserting TIPS in a blood vessel that relates to liver function. Additionally, variable flow stents, including adjustable variable flow stents, may be used in other medical procedures and in other vascular vessels according to the teachings and embodiments described herein. Non-limiting examples include a variable diameter stent as described herein for use with a dialysis graft or to treat a fistula, for example an arteriovenous (AV) fistula.

As will be understood by those familiar with the art, the invention may be embodied in other specific forms without departing from the spirit or essential characteristics thereof. Likewise, the particular naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

While the invention has been described in terms of several embodiments, those of ordinary skill in the art will recognize that the invention is not limited to the embodiments described but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A variable flow stent comprising:
    a cylindrical wire mesh;
    a cylindrical cover attached to an interior of the cylindrical wire mesh;
    an expandable secondary chamber in the cylindrical cover;
    a self-healing valve in the cylindrical cover and coupled to the secondary chamber; and
    a radiopaque collar concentrically disposed around the self-healing valve.

2. The variable flow stent of claim 1, wherein the secondary chamber is configured to be inflated via the self-healing valve.

3. The variable flow stent of claim 2, wherein the secondary chamber is configured to be inflated via a percutaneously inserted catheter that engages with the self-healing valve.

4. The variable flow stent of claim 3, wherein the catheter comprises a side firing curved needle that engages with the self-healing valve to inflate the secondary chamber.

5. The variable flow stent of claim 1, wherein the self-healing valve comprises a self-healing membrane.

6. The variable flow stent of claim 1, wherein the variable flow stent is configured to controllably limit blood flow in a transjugular intrahepatic portosystemic shunt (TIPS).

7. The variable flow stent of claim 1, wherein the variable flow stent is configured to controllably limit blood flow in a dialysis graft or a fistula.

8. A system comprising:
    a variable flow stent comprising:
    a cylindrical wire mesh having an interior stent cover;
    an expandable chamber in the interior stent cover;
    a self-healing valve disposed in an interior wall of the stent cover and in fluid communication with the expandable chamber; and
    a radiopaque collar concentrically disposed around the self-healing valve; and
    a catheter comprising a balloon insertable into the expandable chamber;
    wherein the balloon is configured to be inserted through the self-healing valve into the expandable chamber and expand the expandable chamber.

9. The system of claim 8, wherein the self-healing valve comprises a self-healing membrane.

10. The system of claim 8, wherein the balloon is configured to be inserted through the self-healing valve via a side-firing needle, and wherein the side-firing needle comprises a shape memory material.

11. A method for deploying a variable flow stent in a blood vessel comprising:
    inserting a stent having an interior stent cover in the blood vessel, the interior stent cover comprising an inflatable secondary chamber and a self-healing valve coupled to the secondary chamber, wherein a radiopaque collar is concentrically disposed around the self-healing valve;
    inserting a catheter percutaneously into the blood vessel;
    delivering an inflation device through the catheter;
    locating the self-healing valve using the radiopaque collar;
    penetrating the self-healing valve with the inflation device;
    inflating the secondary chamber using the inflation device; and,
    withdrawing the catheter and inflation device from the blood vessel.

12. The method of claim 11, wherein the inflation device comprises a curved needle.

13. The method of claim 12, wherein the curved needle comprises NITINOL.

14. The method of claim 11, wherein the inflation device comprises a balloon insertable into the secondary chamber.

15. The method of claim 11, wherein the self-healing valve comprises a self-healing membrane.

16. The method of claim 11, wherein the inflation device is a percutaneously inserted needle.

* * * * *